United States Patent
Carli

(10) Patent No.: US 7,892,266 B2
(45) Date of Patent: Feb. 22, 2011

(54) BONE ANCHORING DEVICE WITH SPHERICAL ARTICULATION

(75) Inventor: Olivier Carli, Geneva (CH)

(73) Assignee: Alphatec Spine, Inc., Carlsbad, CA (US)

(*) Notice: Subject to any disclaimer, the term of this patent is extended or adjusted under 35 U.S.C. 154(b) by 0 days.

(21) Appl. No.: 10/520,961

(22) PCT Filed: Jul. 10, 2003

(86) PCT No.: PCT/FR03/02167

§ 371 (c)(1),
(2), (4) Date: Oct. 25, 2005

(87) PCT Pub. No.: WO2004/006791

PCT Pub. Date: Jan. 22, 2004

(65) Prior Publication Data

US 2006/0111718 A1 May 25, 2006

(30) Foreign Application Priority Data

Jul. 12, 2002 (FR) .................... 02 08838

(51) Int. Cl.
*A61B 17/86* (2006.01)
(52) U.S. Cl. ..................... 606/301
(58) Field of Classification Search .......... 606/61, 606/70, 71, 72, 73; 403/122–123
See application file for complete search history.

(56) References Cited

U.S. PATENT DOCUMENTS

| | | | |
|---|---|---|---|
| 2,112,007 A * | 3/1938 | Adams | 433/174 |
| 4,055,385 A * | 10/1977 | Bjors | 411/378 |
| 4,836,196 A | 6/1989 | Park et al. | |
| 5,086,797 A * | 2/1992 | Earnshaw et al. | 135/20.1 |
| 5,129,899 A | 7/1992 | Small et al. | |
| 5,234,431 A | 8/1993 | Keller | |
| 5,474,551 A | 12/1995 | Finn et al. | |
| 5,545,163 A | 8/1996 | Miller et al. | |
| 5,582,612 A | 12/1996 | Lin | |
| 5,591,166 A * | 1/1997 | Bernhardt et al. | 606/266 |
| 5,613,968 A | 3/1997 | Lin | |
| 5,628,740 A * | 5/1997 | Mullane | 606/61 |
| 5,800,435 A * | 9/1998 | Errico et al. | 606/61 |
| 5,925,047 A | 7/1999 | Errico et al. | |
| 5,954,725 A | 9/1999 | Sherman et al. | |
| 5,984,924 A | 11/1999 | Asher et al. | |
| 6,050,997 A | 4/2000 | Mullane | |
| 6,267,765 B1 | 7/2001 | Taylor et al. | |
| 6,287,309 B1 | 9/2001 | Baccelli et al. | |
| 6,309,391 B1 * | 10/2001 | Crandall et al. | 606/61 |
| 6,413,258 B1 | 7/2002 | Bernhardt, Jr. | |
| 6,454,769 B2 | 9/2002 | Wagner et al. | |
| 6,520,963 B1 | 2/2003 | McKinley | |
| 6,569,164 B1 | 5/2003 | Assaker et al. | |
| 6,610,062 B2 | 8/2003 | Bailey et al. | |

(Continued)

*Primary Examiner*—Thomas C Barrett
*Assistant Examiner*—Nicholas Woodall
(74) *Attorney, Agent, or Firm*—Michael R. Shevlin

(57) ABSTRACT

A bone anchoring device includes a bone anchoring element provided with a head for receiving a threaded shaft on which a clamping means is to be screwed. A spherical articulation is provided between the bone anchoring element and the threaded shaft to provide the threaded shaft with multiple orientations, and a rotational linkage is also provided between the bone anchoring element and the threaded shaft.

12 Claims, 1 Drawing Sheet

U.S. PATENT DOCUMENTS

| | | | |
|---|---|---|---|
| 6,623,485 B2 * | 9/2003 | Doubler et al. | 606/61 |
| 6,641,583 B2 | 11/2003 | Shluzas et al. | |
| 6,663,635 B2 | 12/2003 | Frigg et al. | |
| 6,676,661 B1 | 1/2004 | Benlloch et al. | |
| 6,682,532 B2 | 1/2004 | Johnson et al. | |
| 6,709,434 B1 | 3/2004 | Gournay et al. | |
| 6,716,214 B1 | 4/2004 | Jackson | |
| 6,800,079 B2 | 10/2004 | Reed | |
| 6,858,031 B2 | 2/2005 | Morrison et al. | |
| 6,887,242 B2 | 5/2005 | Doubler et al. | |
| 7,028,699 B2 * | 4/2006 | Lee | 135/20.1 |
| 7,037,022 B2 * | 5/2006 | Schonhoff et al. | 403/114 |
| 2002/0111626 A1 | 8/2002 | Ralph et al. | |
| 2003/0163133 A1 * | 8/2003 | Altarac et al. | 606/61 |
| 2004/0006342 A1 * | 1/2004 | Altarac et al. | 606/61 |
| 2004/0102781 A1 | 5/2004 | Jeon | |
| 2004/0138661 A1 | 7/2004 | Bailey | |
| 2004/0236330 A1 | 11/2004 | Purcell et al. | |
| 2005/0049588 A1 | 3/2005 | Jackson et al. | |
| 2005/0080415 A1 | 4/2005 | Keyer et al. | |
| 2005/0080420 A1 | 4/2005 | Farris et al. | |
| 2006/0052783 A1 * | 3/2006 | Dant et al. | 606/61 |
| 2006/0106382 A1 * | 5/2006 | Gournay et al. | 606/61 |

* cited by examiner

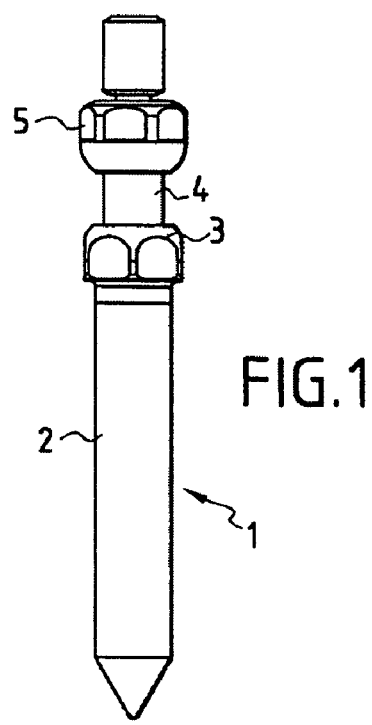
FIG.1
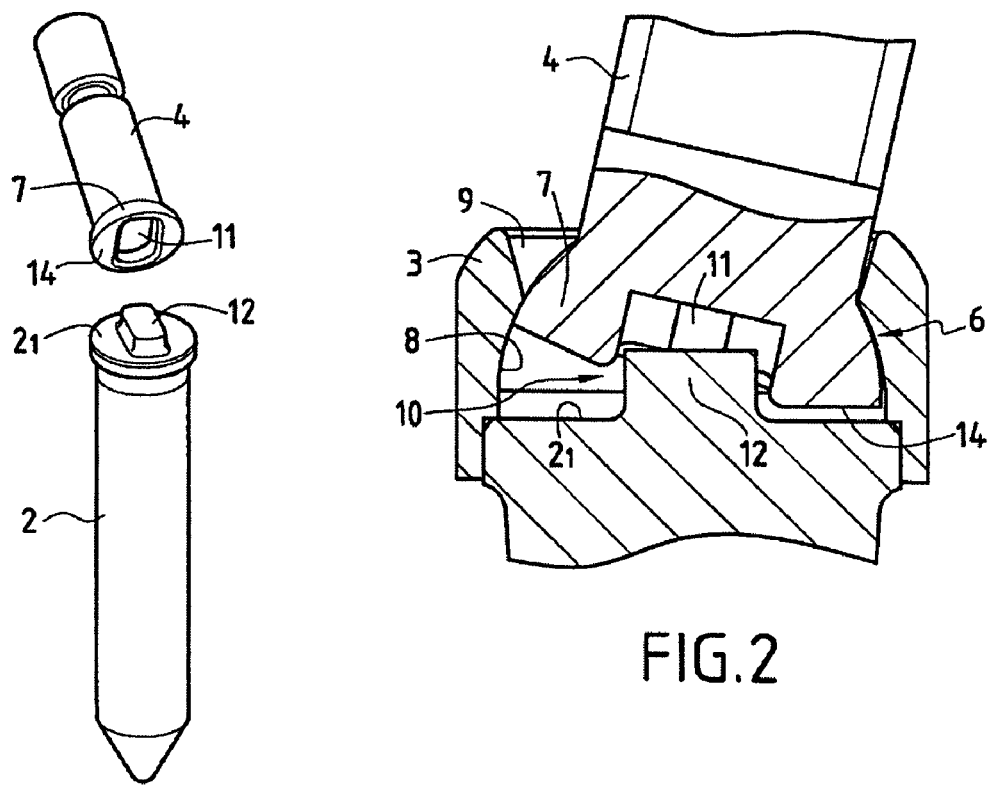
FIG.2
FIG.3

BONE ANCHORING DEVICE WITH SPHERICAL ARTICULATION

CROSS-REFERENCE TO RELATED APPLICATIONS

This application claims the benefit of International Patent Application No. PCT/FR2003/002167, filed Jul. 10, 2003, which claims priority to French Patent Application No. 02/08 838 filed Jul. 12, 2002, the disclosure of which is hereby incorporated herein in its entirety by reference.

FIELD OF THE INVENTION

The present invention relates to the technical field of osteosynthesis notably of the vertebral column and more specifically it is directed to an anchoring device in vertebrae, used in osteosynthesis systems for the vertebral column.

More specifically, the object of the invention is directed to a bone anchoring device, such as an anchoring screw in order to have a relative angulation with an osteosynthesis system implementing a linkage rod for example.

BACKGROUND OF THE INVENTION

One of the known applications of the object of the invention relates to systems designed for correcting and stabilizing the vertebral column and for facilitating bone fusion at different levels of the vertebral column. According to such an application, such a system includes an intervertebral linkage element such as a rod or a plate able to be bent and positioned along the vertebral column while being held in position by screws implanted in the vertebrae in order to follow the curvature of the region of the fitted-out vertebral column. Hence, in order to comply with the anatomy of the vertebral column, the linkage rod should be conformed in order to have large angulations notably for its mounting relatively to the lumbar and sacral vertebrae.

In order to allow such conformations of the rod while ensuring its effective locking relatively to the anchoring screws, fitting out the anchoring screws with a spherical articulation for receiving the linkage rod is known for allowing an adaptive relative angulation between the anchoring screw and the intervertebral linkage element.

SUMMARY OF THE INVENTION

Many anchoring devices of the spherical articulation type have been proposed in the state of the art. Thus, a bone anchoring device is known, which includes a bone anchoring element such as a screw provided with a head for receiving a threaded shaft whereon a clamping means of a linkage rod is designed to be screwed. A spherical articulation is provided between the bone anchoring element and the threaded shaft so as to provide the threaded shaft with multiple orientations. According to an exemplary embodiment, the end of the threaded shaft includes means for receiving an ancillary allowing rotational locking of the threaded shaft during the operation for screwing or unscrewing of the clamping nut on the threaded shaft. It thus appears that the operation for screwing or unscrewing the nut on the threaded shaft is an operation requiring the use of different ancillaries, which complicates and lengthens the operation for placing an osteosynthesis system.

A bone anchoring device is also known from U.S. Pat. No. 5,628,740, including a bone anchoring element provided with a head for receiving a threaded shaft whereon a clamping means is designed to be screwed. A spherical articulation is provided between the bone anchoring element and the threaded shaft. The threaded shaft includes two diametrically opposite studs engaging with grooves provided in the head fitting the bone anchoring element. Theses studs cooperate with grooves to allow the pivoting of the threaded shaft.

Multiple orientation of the threaded shaft relatively to the bone anchoring element cannot be maintained with such a device, while providing effective rotational linkage, between the bone anchoring element and the threaded shaft.

The object of the invention is therefore directed to remedy the drawbacks of the prior art by proposing a bone anchoring device with which screwing or even unscrewing of a clamping nut on the threaded shaft may be provided simply and securely, otherwise maintaining its multiple orientation function for the threaded shaft.

To achieve such goals, the bone anchoring device according to the invention includes a bone anchoring element provided with a head for receiving a threaded shaft upon which a clamping means is designed to be screwed, a spherical articulation being provided between the bone anchoring element and the threaded shaft to allow for multiple orientation of the threaded shaft. According to the invention, the bone anchoring device includes rotational linkage means between the bone anchoring element and the threaded shaft, while maintaining multiple orientation of the threaded shaft relatively to the bone anchoring element.

BRIEF DESCRIPTION OF THE DRAWINGS

For a fuller understanding of the invention, reference is made to the following detailed description, taken in connection with the accompanying drawings illustrating various embodiments of the present invention, in which FIG. 1 is schematic view of an exemplary embodiment of a bone anchoring device according to the invention;

FIG. 2 is an elevation sectional view at a larger scale of the exemplary embodiment illustrated in FIG. 1;

FIG. 3 is a partial perspective view showing a characteristic feature of the object of the invention.

DETAILED DESCRIPTION OF THE PREFERRED EMBODIMENTS

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout, and prime notation is used to indicate similar elements in alternate embodiments.

As it is apparent in the figures, the object of the invention relates to a bone anchoring device 1 intended to be implanted in the vertebral column. Such a bone anchoring device 1 includes a bone anchoring element 2, broadly speaking, suitable for being made in different known ways. The bone anchoring element 2 may exist as a hook, a plate or an anchoring screw such as illustrated in the drawings. This bone anchoring element 2 is provided with a head 3 for receiving a threaded shaft 4 whereon a clamping means 5 is designed to be screwed. Conventionally, a spherical articulation 6 is provided between the bone anchoring element 2 and the threaded shaft 4 in order to allow multiple orientation of the threaded shaft 4 relatively to the bone anchoring element 2.

In the illustrated exemplary embodiment, the threaded shaft 4 at the opposite end of its free end, is provided with a ball-and-socket joint 7 of hemispherical shape mounted on the inside of a housing 8 with a complementary shape in order to form the spherical articulation 6. In the illustrated example, the housing 8 is provided inside the receiving head 3 which exists as a grip nut for a screwing tool. This receiving head 3 which, for example, is reported as being fixed on the bone anchoring element 2, includes an aperture 9 opening into the housing 8 in order to allow the passage of the threaded shaft 4 and its multiple orientation angular displacement relatively to the bone anchoring element 2. Of course, provision may be made for making the ball-and-socket joint 7 on the end of the bone anchoring element 2 and the housing 8 on the threaded shaft 4.

According to the invention, the bone anchoring device 1 includes rotational linkage means 10 between the bone anchoring element 2 and the threaded shaft 4. In other words, the bone anchoring element 2 and the threaded shaft 4 are directly linked in rotation while maintaining multiple orientation for the threaded shaft 4 relatively to the bone anchoring element 2. In this respect, the linkage means 10 are made outside the spherical articulation 6.

As it is more specifically apparent from FIGS. 2 and 3, the rotational linkage means 10 consist of a geometrical form or female imprint 11 cooperating with a complementary geometrical form or male imprint 12. One of the geometrical forms 11, 12 is provided on the receiving head 3 of the bone anchoring element 2 whereas the other geometrical form is made on the end of the threaded shaft 4.

These female 11 and male 12 geometrical forms are said to be complementary in the sense that a rotational force exerted along the axis of the bone anchoring element 2 or of the threaded shaft 4 leads to rotational locking between the bone anchoring element 2 and the threaded shaft 4, regardless of the relative orientation between these two parts. Such rotational locking is directly obtained between the bone anchoring element 2 and the threaded shaft 4 without the help of other parts. It should therefore be contemplated that the female 11 and male 12 geometrical forms may have transverse cross-sections with identical or different shapes. In the illustrated exemplary embodiment and as apparent from FIG. 3, the transverse cross-sections of the female 11 and male 12 geometrical forms are substantially rectangular. Of course, the female 11 and male 12 geometrical forms may have sections with different shapes, such as elliptical, oval, non-circular shapes with at least one edge, etc. The female geometrical form 11 is provided by a cavity or housing whereas the male geometrical form 12 is achieved by a stud or a protruding portion.

As it is apparent from the above, the female 11 and male 12 geometrical forms delimit clearance between them to allow multiple orientation between the threaded shaft 4 and the bone anchoring element 2 while providing rotational linkage between the male and female geometrical forms.

Preferably, it should be noted that the transverse face 14 delimiting the ball-and-socket joint 7 and the end face $2_1$ of the bone anchoring element 4 extend, facing each other and at a distance from one another, in order to allow multiple orientation of the threaded shaft 4. Advantageously, the transverse face 14 of the ball-and-socket joint 7 and/or the end face $2_1$ of the bone anchoring element 2 have a convex shape in order to allow such an orientation with limited bulkiness.

One of the geometrical forms, i.e., the male geometrical form 12 in the illustrated example is provided on the end of the bone anchoring element 2 whereas the female geometrical form 11 is provided at the free end of the threaded shaft 4. More specifically, the female geometrical form 11 is made in the transverse face 14 delimiting the hemispherical ball-and-socket joint 7, whereas the male geometrical shape 12 is made on the end face $2_1$ of the bone anchoring element 2. Of course, the position of the male and female geometrical forms on the threaded shaft and on the bone anchoring element may be reversed.

The anchoring device 1 according to the invention therefore has a spherical articulation thereby allowing an adaptive relative angulation between the bone anchoring element 2 and a member of an osteosynthesis system such as a linkage rod. The fixing of this linkage rod via a clamping means 5 is achieved in a simple way without having to resort to an ancillary to hold the threaded shaft 4 in position in so far as the latter may not rotate because of the anchoring of element 2 and of the presence of the rotational linkage means 10.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. A bone anchoring device comprising:
   a bone anchoring element provided with a head having a first end face and defining a longitudinal axis;
   a threaded shaft having a second end face at an end thereof facing the first end face of the bone anchoring element;
   a clamping means screwed to the head of the bone anchoring element for holding the threaded shaft in a longitudinal relation to the bone anchoring element;
   a spherical articulation provided between the bone anchoring element and the threaded shaft in order to allow multiple orientation of the threaded shaft, wherein contact between the first and second end faces delimit the extent of movement of the spherical articulation; and
   rotational linkage means situated on the longitudinal axis and between the bone anchoring element and the threaded shaft permitting spherical articulation between the bone anchoring element and the threaded shaft, and rotational force exerted along an axis of the bone anchoring element or of the threaded shaft leads to rotational locking between the bone anchoring element and the threaded shaft, regardless of the multiple orientation of the threaded shaft relative to the bone anchoring element,
   wherein the rotational linkage means comprises a female geometrical form cooperating with a complimentary male geometrical form, delimiting therebetween a clearance in order to allow multiple orientation between the threaded shaft and the bone anchoring element, the female and male geometrical forms having non-circular transverse cross-sections.

2. The bone anchoring device according to claim 1, wherein the rotation linkage means are provided outside the spherical articulation.

3. The bone anchoring device according to claim 1, wherein one of the geometrical forms is provided on the head of the bone anchoring element, and wherein the other geometrical form is provided on the end of the threaded shaft.

4. The bone anchoring device according to claim 1 wherein one of the geometrical shapes is provided on the end face of the bone anchoring element, extending within an open housing provided in the head and receiving the end of the threaded shaft made as a ball-and-socket joint in order to form the spherical articulation, said ball-and-socket joint being provided with the other geometrical form on the transverse face.

5. The bone anchoring device according to claim 4, wherein the transverse face of the ball-and-socket joint and the end face of the bone anchoring element extend a distance from one another in order to allow multiple orientation of the threaded shaft.

6. The bone anchoring device according to claim 5, wherein at least one of the transverse face of the ball-and-socket joint and the end face of the bone anchoring element has a convex shape.

7. The bone anchoring device according to claim 4, wherein the male geometrical form is made on the end of the bone anchoring element, and wherein the female geometrical form is provided on the ball-and-socket joint.

8. The bone anchoring device according to claim 1, wherein the head forms a grip nut for a screwing tool.

9. A bone anchoring device comprising:
a bone anchoring element provided with a head and defining a longitudinal axis;
a threaded shaft;
a clamping means screwed to said head of the bone anchoring element for holding the threaded shaft in longitudinal relation to the bone anchoring element;
a spherical articulation provided between the bone anchoring element and the threaded shaft in order to allow multiple orientation of the threaded shaft relative to the bone anchoring element; and
rotational linkage means situated on the longitudinal axis between the bone anchoring element and the threaded shaft permitting the spherical articulation between the bone anchoring element and the threaded shaft and rotational force exerted along an axis of the bone anchoring element or of the threaded shaft leads to rotational locking between the bone anchoring element and the threaded shaft, regardless of the multiple orientation of the threaded shaft relative to the bone anchoring element,
wherein the rotational linkage means comprises a female non-circular geometrical form on the longitudinal axis cooperating with a complementary non-circular male geometrical form on the longitudinal axis, delimiting therebetween a clearance in order to allow multiple orientation between the threaded shaft and the anchoring element.

10. A bone anchoring device comprising:
a bone anchoring element provided with a head having a first end face and defining a longitudinal axis;
a threaded shaft having a second end face at an end thereof facing the first end face of the bone anchoring element;
a clamping means screwed to the head of the bone anchoring element for holding the threaded shaft in longitudinal relation to the bone anchoring element;
a spherical articulation provided between the bone anchoring element and the threaded shaft in order to allow multiple orientation of the threaded shaft, wherein contact between the first and second end faces delimit the extent of movement of the spherical articulation; and
rotational linkage means situated on the longitudinal axis and between the bone anchoring element and the threaded shaft permitting spherical articulation between the bone anchoring element and the threaded shaft and rotational force exerted along an axis of the bone anchoring element or of the threaded shaft leads to rotational locking between the bone anchoring element and the threaded shaft, regardless of the multiple orientation of the threaded shaft relative to the bone anchoring element.

11. A bone anchoring device according to claim 10, wherein:
one of said and second end faces is flat.

12. A bone anchoring device according to claim 11, wherein:
the other of said first and second end faces is convex.

* * * * *